United States Patent [19]

Radocy et al.

[11] Patent Number: 5,085,665
[45] Date of Patent: Feb. 4, 1992

[54] PROSTHETIC DEVICE FOR VIGOROUS ACTIVITIES

[76] Inventors: Robert Radocy, 2860 Pennsylvania Ave., Boulder, Colo. 80303; Ronald E. Dick, Magnolia Star Rte. Box 733, Nederland, Colo. 80466

[21] Appl. No.: 395,322
[22] Filed: Jul. 6, 1982
[51] Int. Cl.⁵ .................................................. A61F 2/54
[52] U.S. Cl. .................................................. 623/57
[58] Field of Search .................. 623/57, 27, 28, 29, 623/53, 54, 55, 56, 65

[56] References Cited

U.S. PATENT DOCUMENTS

| | | | |
|---|---|---|---|
| 40,763 | 12/1863 | Marks | 3/12 |
| 831,330 | 9/1906 | Doebrich | 3/12 |
| 1,304,201 | 5/1915 | Blankenship et al. | 3/12 |
| 4,007,496 | 2/1977 | Glabiszewski | 3/12 |

*Primary Examiner*—David J. Isabella
*Attorney, Agent, or Firm*—James E. Pittenger

[57] ABSTRACT

A prosthetic device for duplicating biomechanical action of the human body is disclosed. The device is mountable on a prosthetic appendage such as a prosthetic arm and is particularly suited for use in vigorous activities such as athletics and the like. Various embodiments of the device including a flexible prosthetic hand, a flexible prosthetic joint module and a prosthetic shock absorber device as well as various modifications and combinations thereof are described.

12 Claims, 11 Drawing Sheets

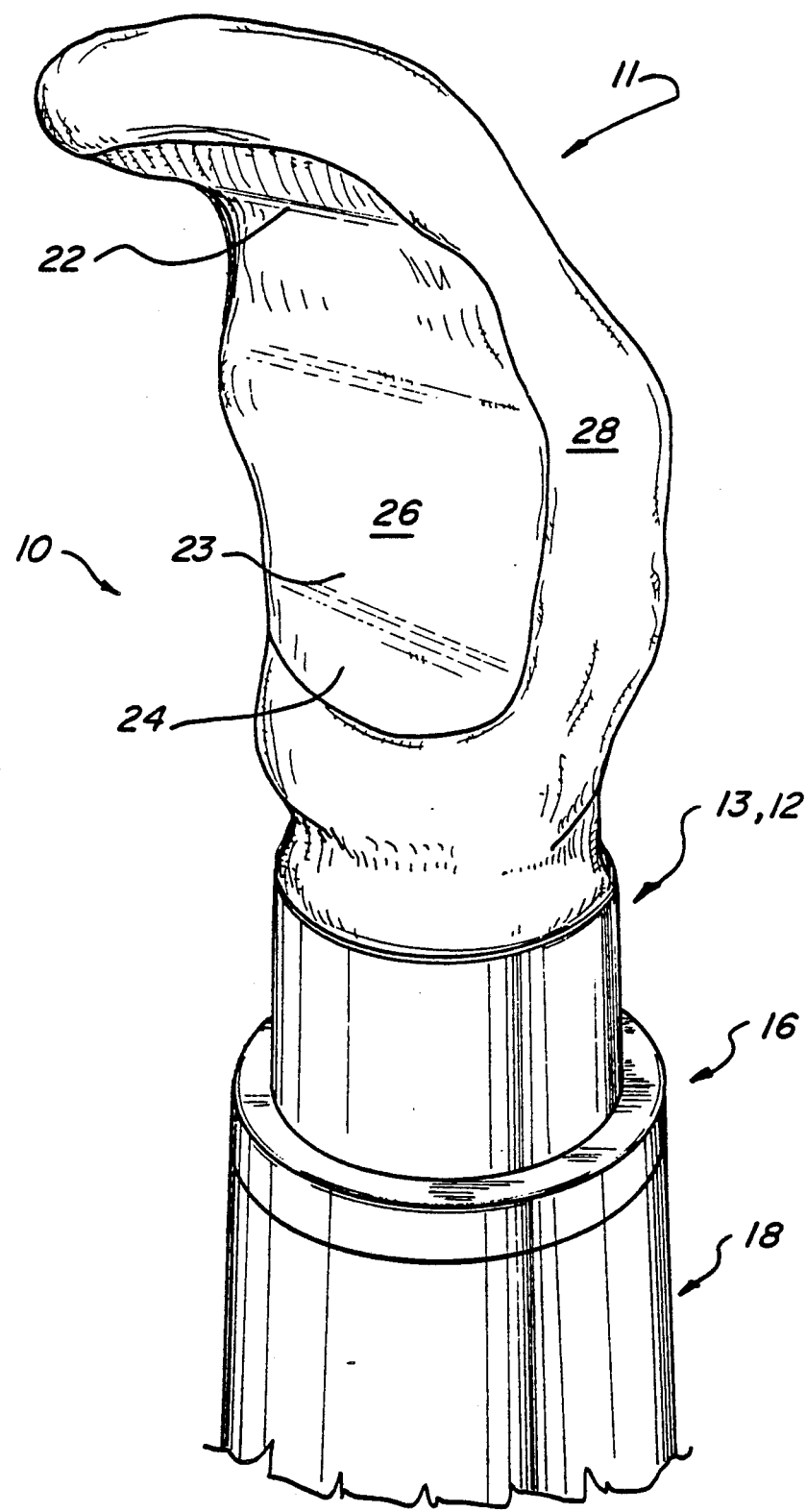
Fig_1

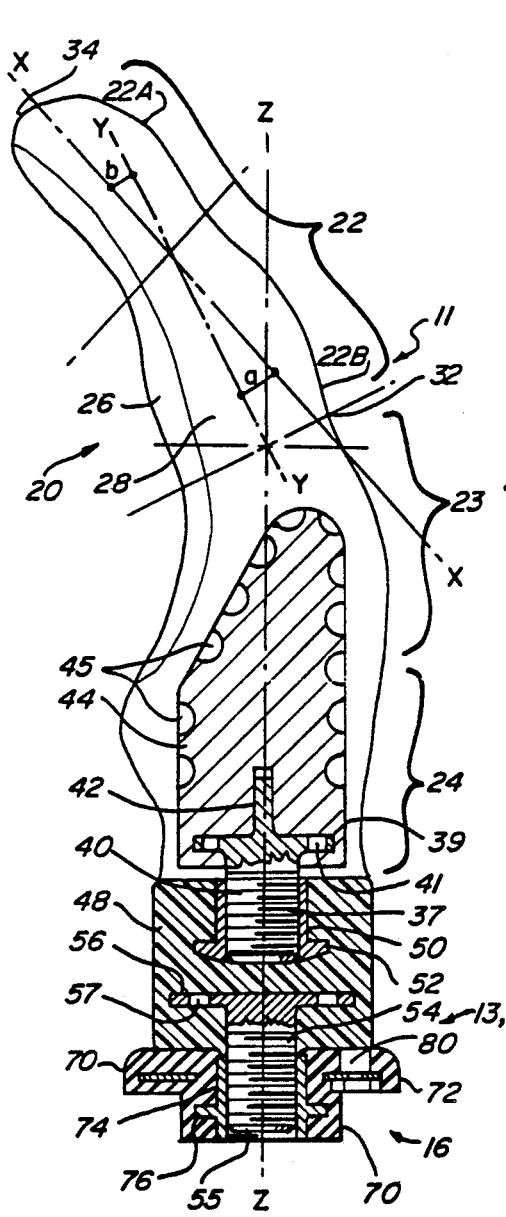
Fig_2
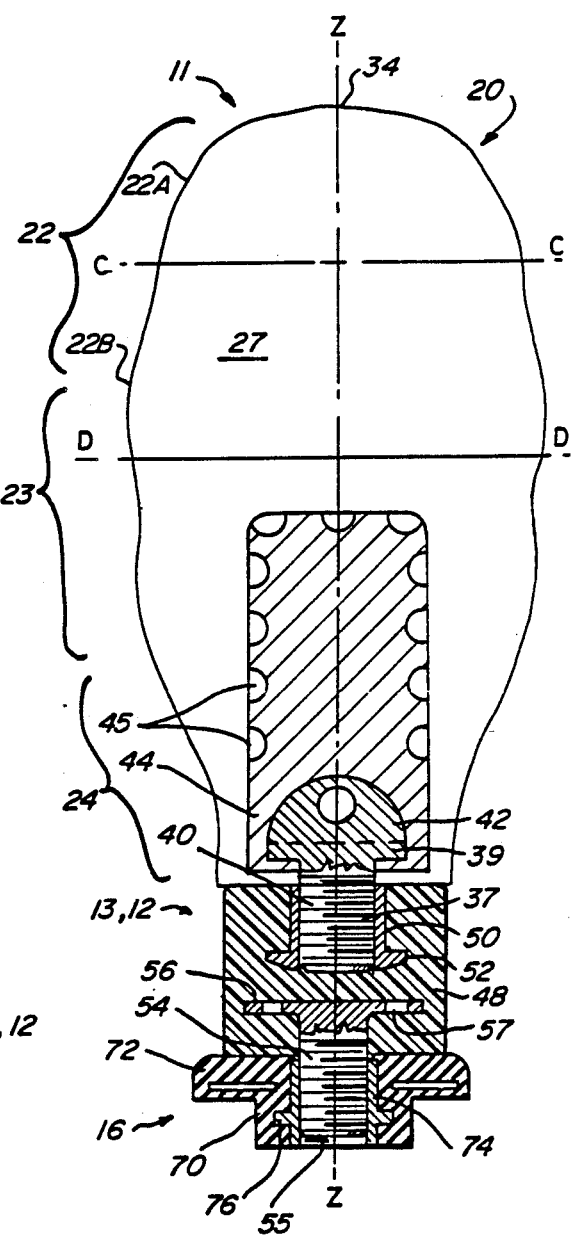
Fig_3

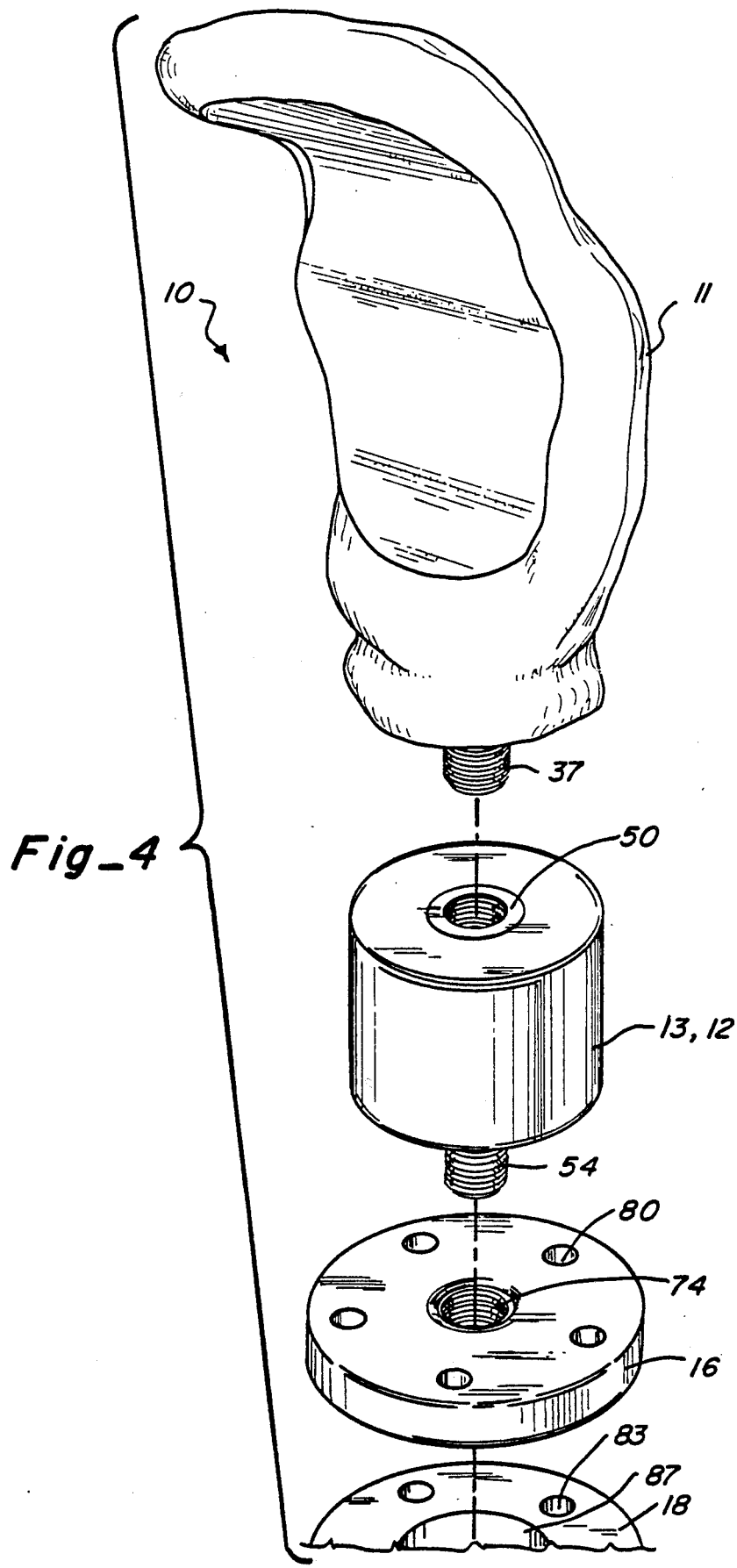
Fig_4

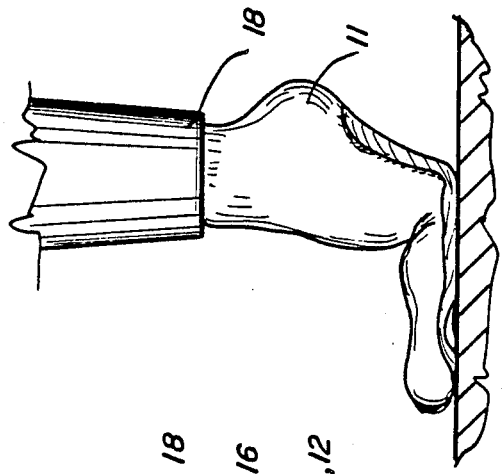
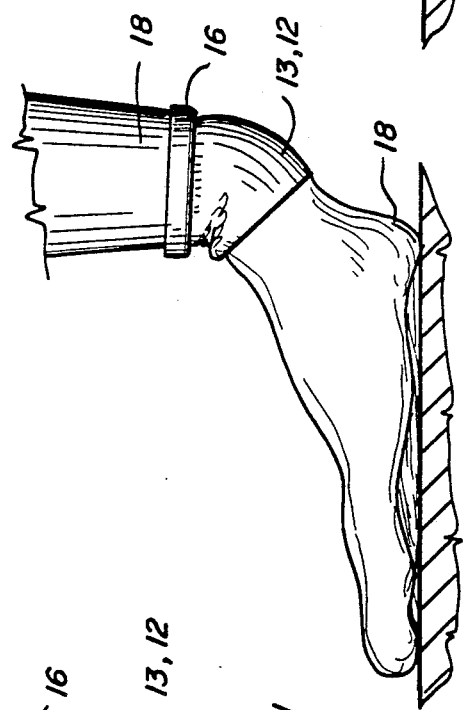
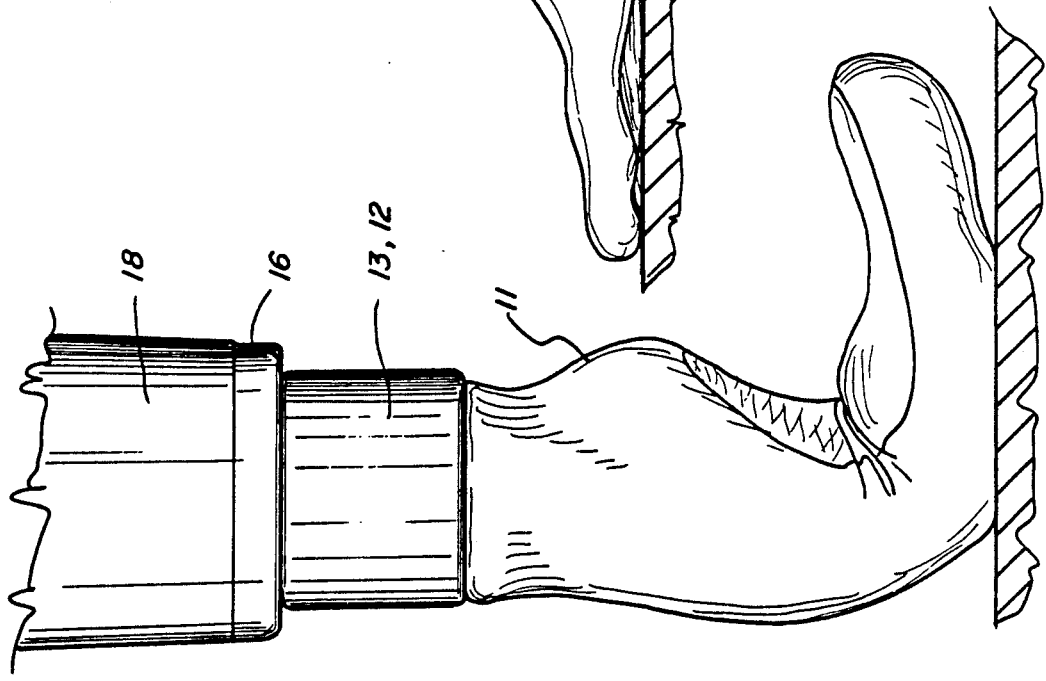

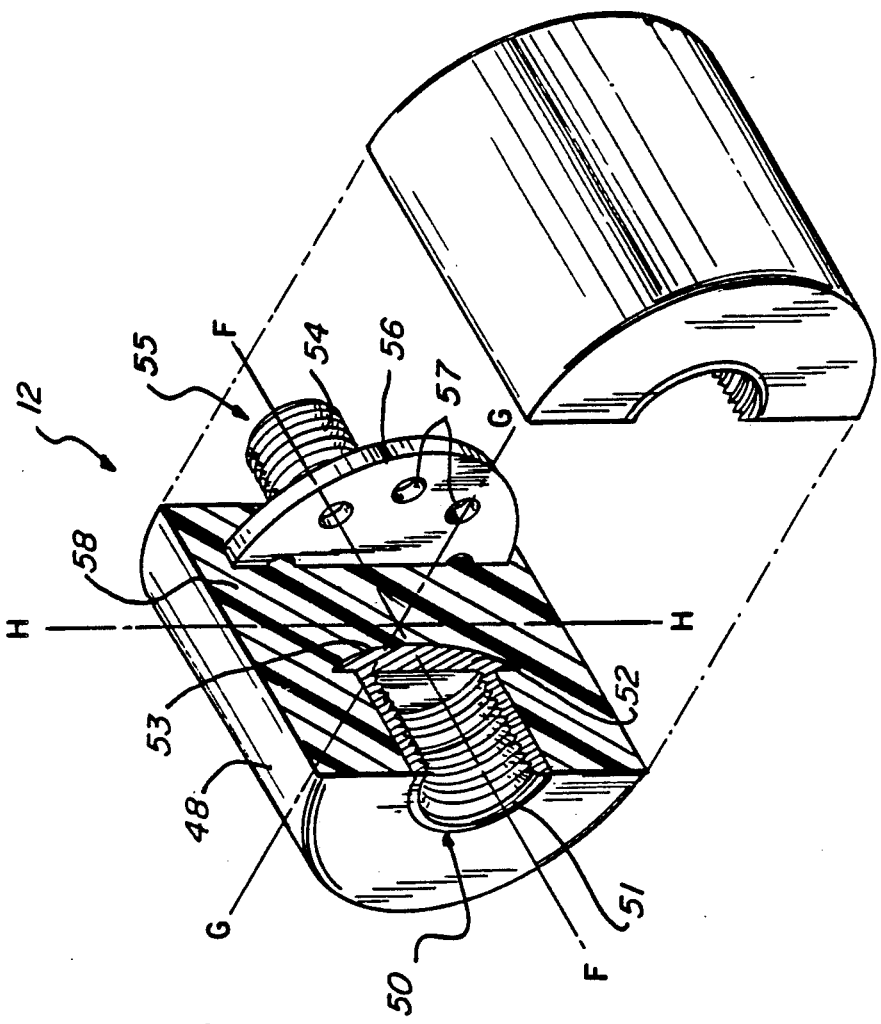
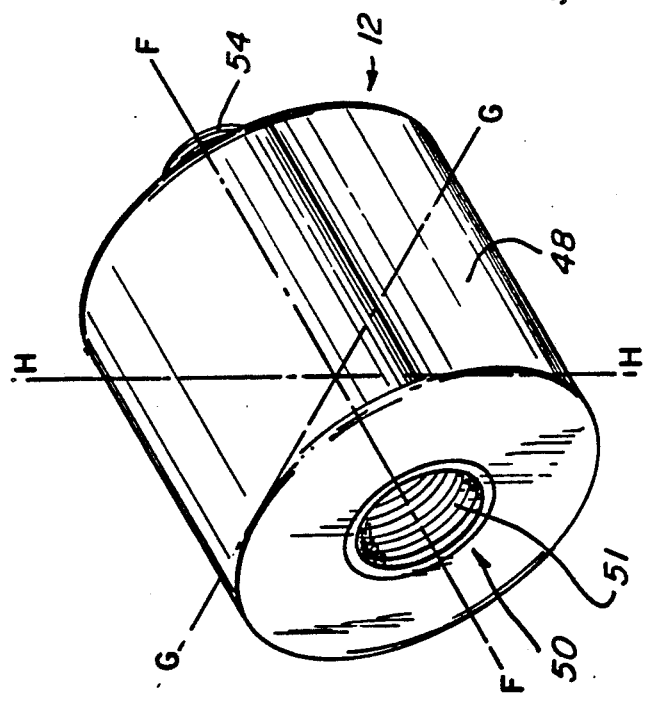
Fig_9
Fig_8

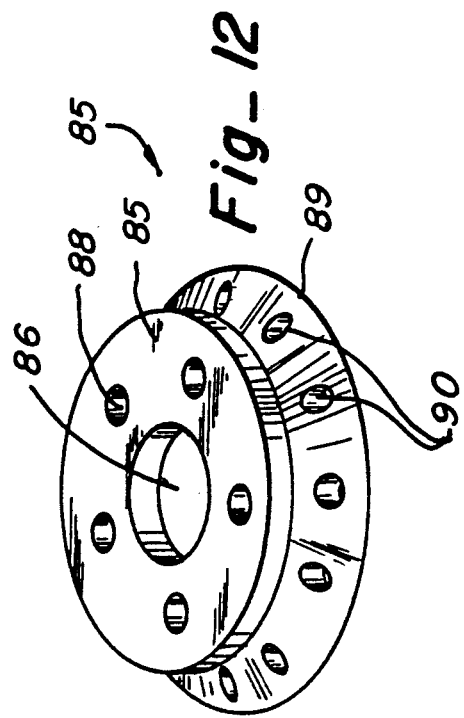
Fig._12
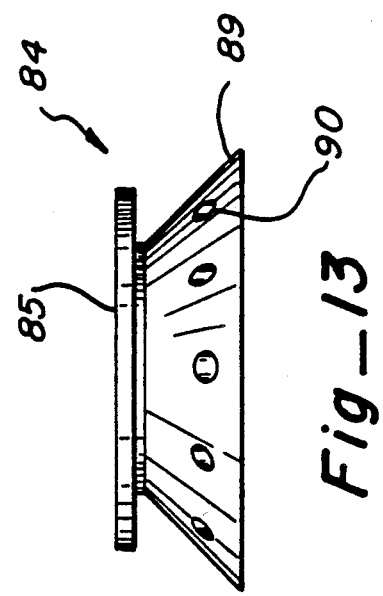
Fig._13
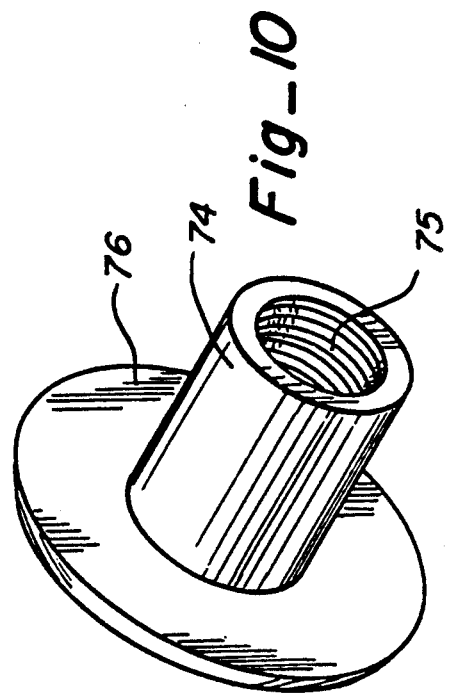
Fig._10
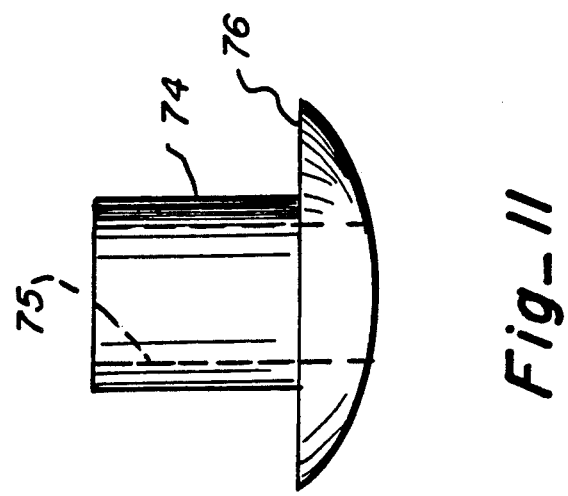
Fig._11

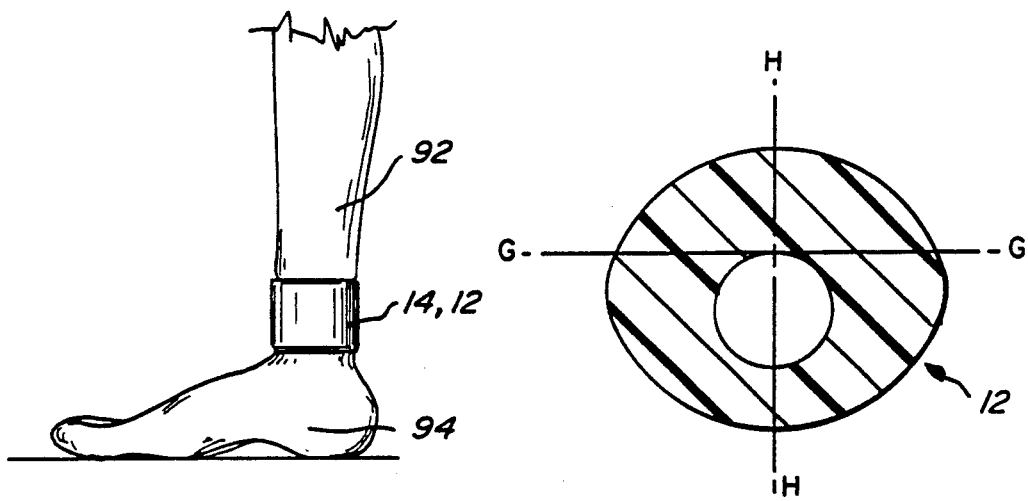
Fig_14  Fig_15
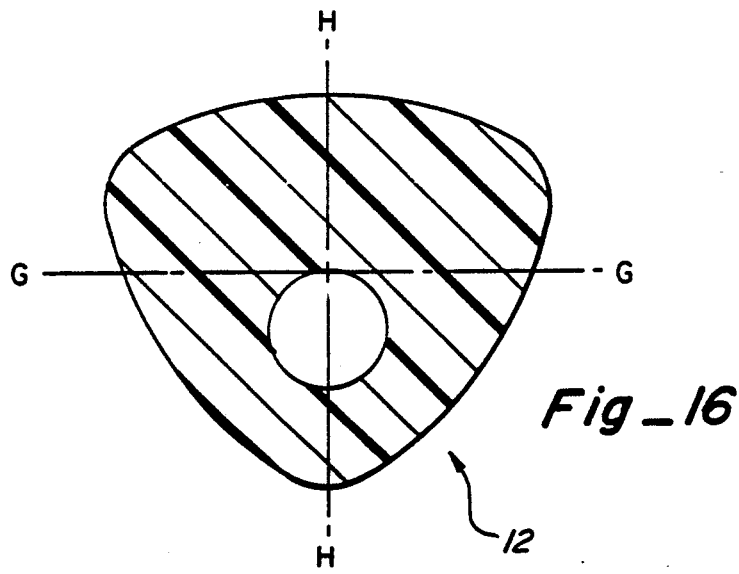
Fig_16
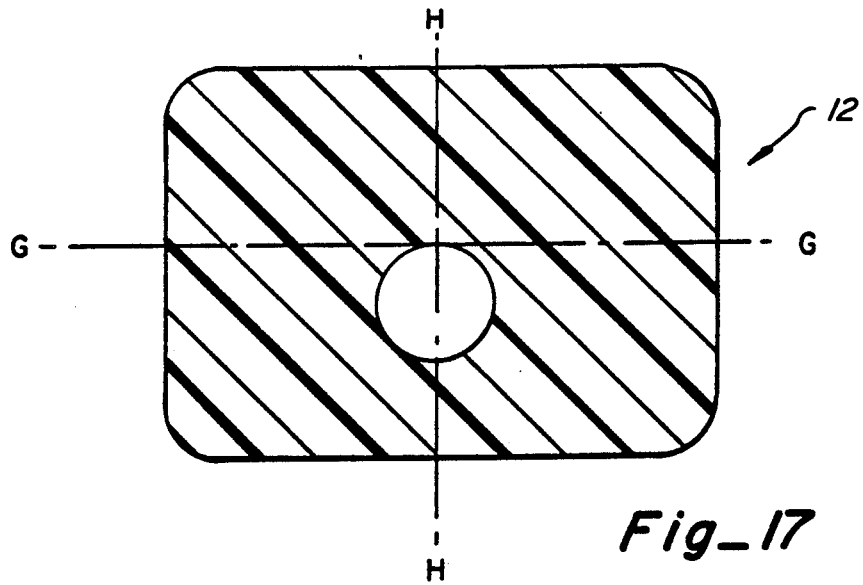
Fig_17

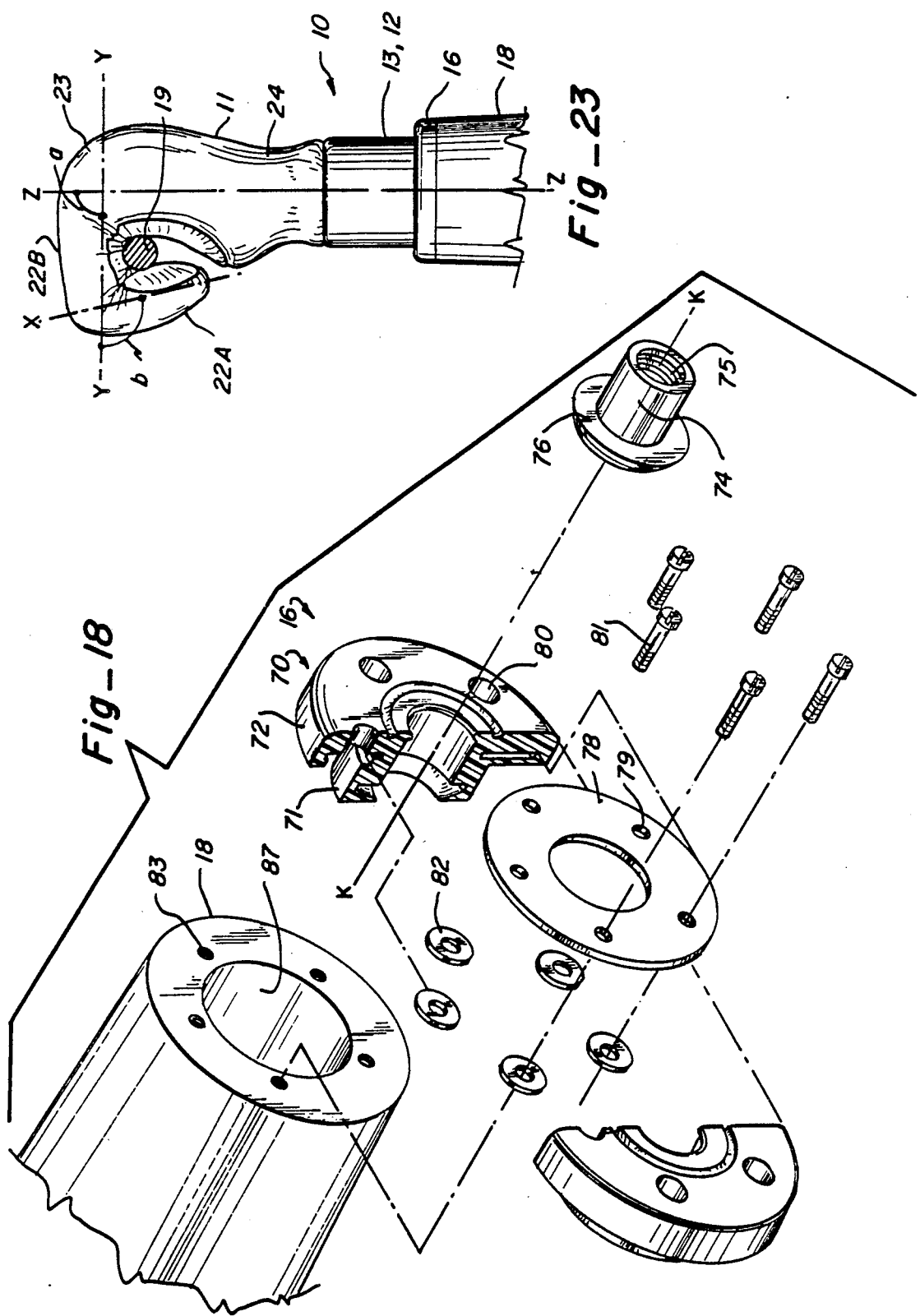

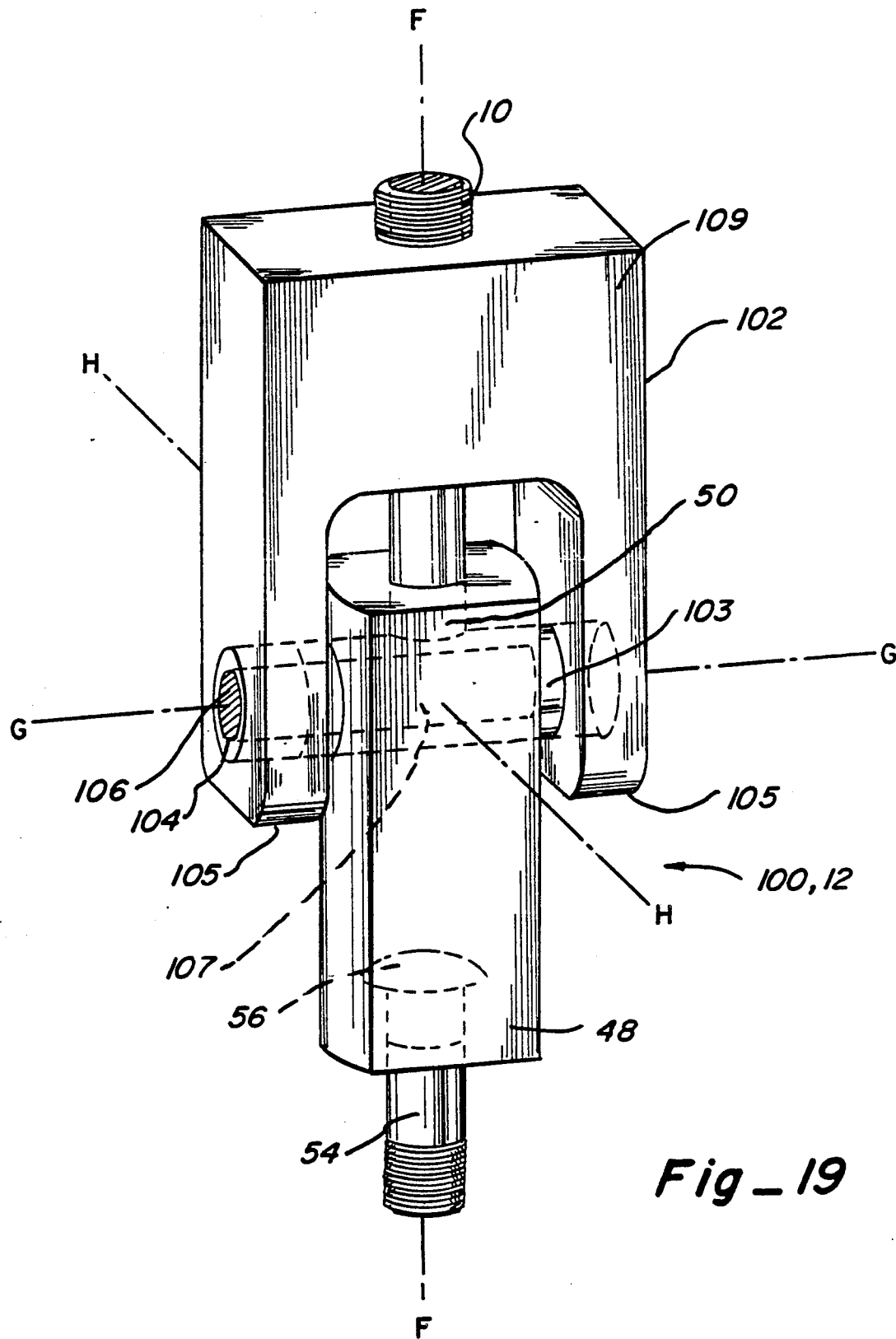
Fig_19

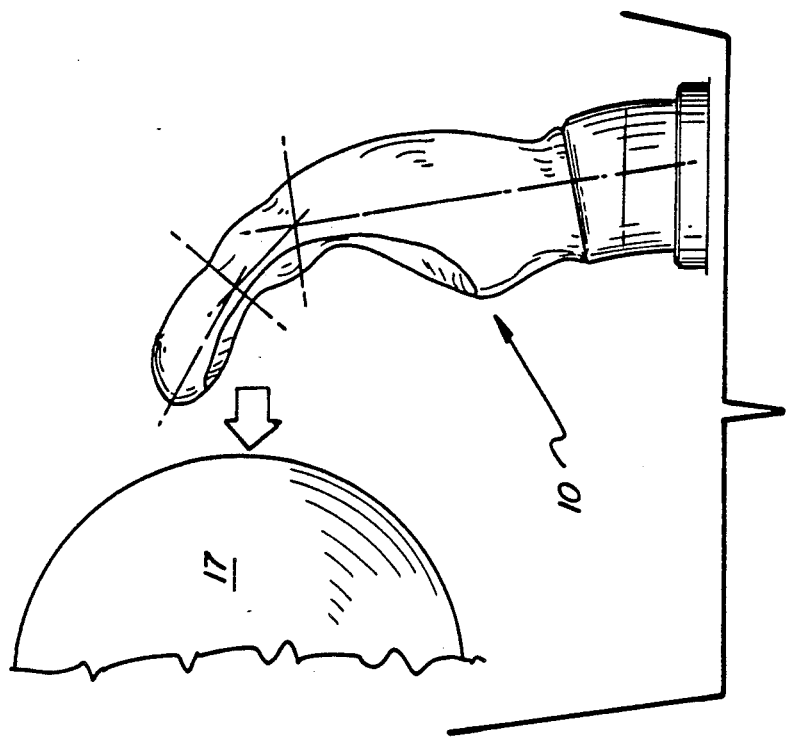
Fig_22
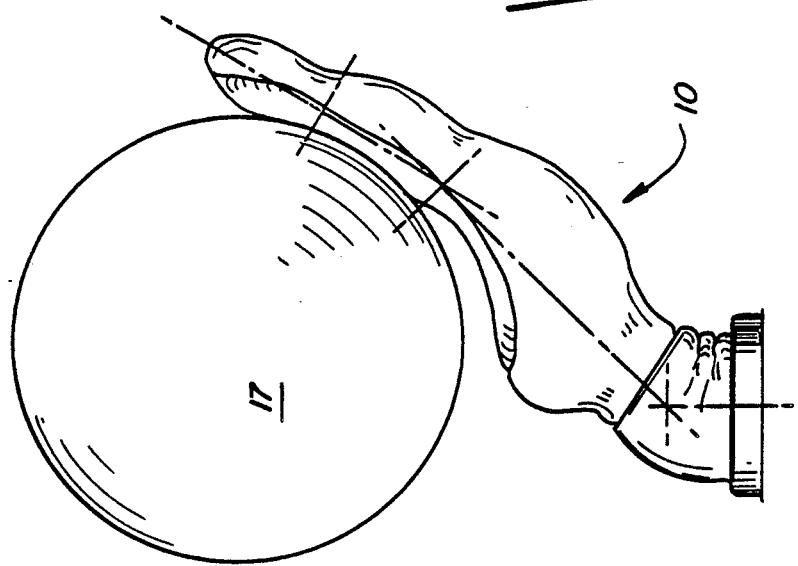
Fig_21
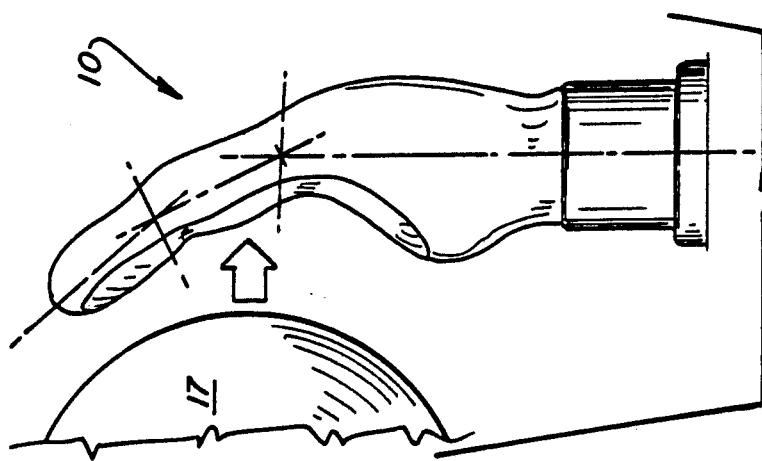
Fig_20

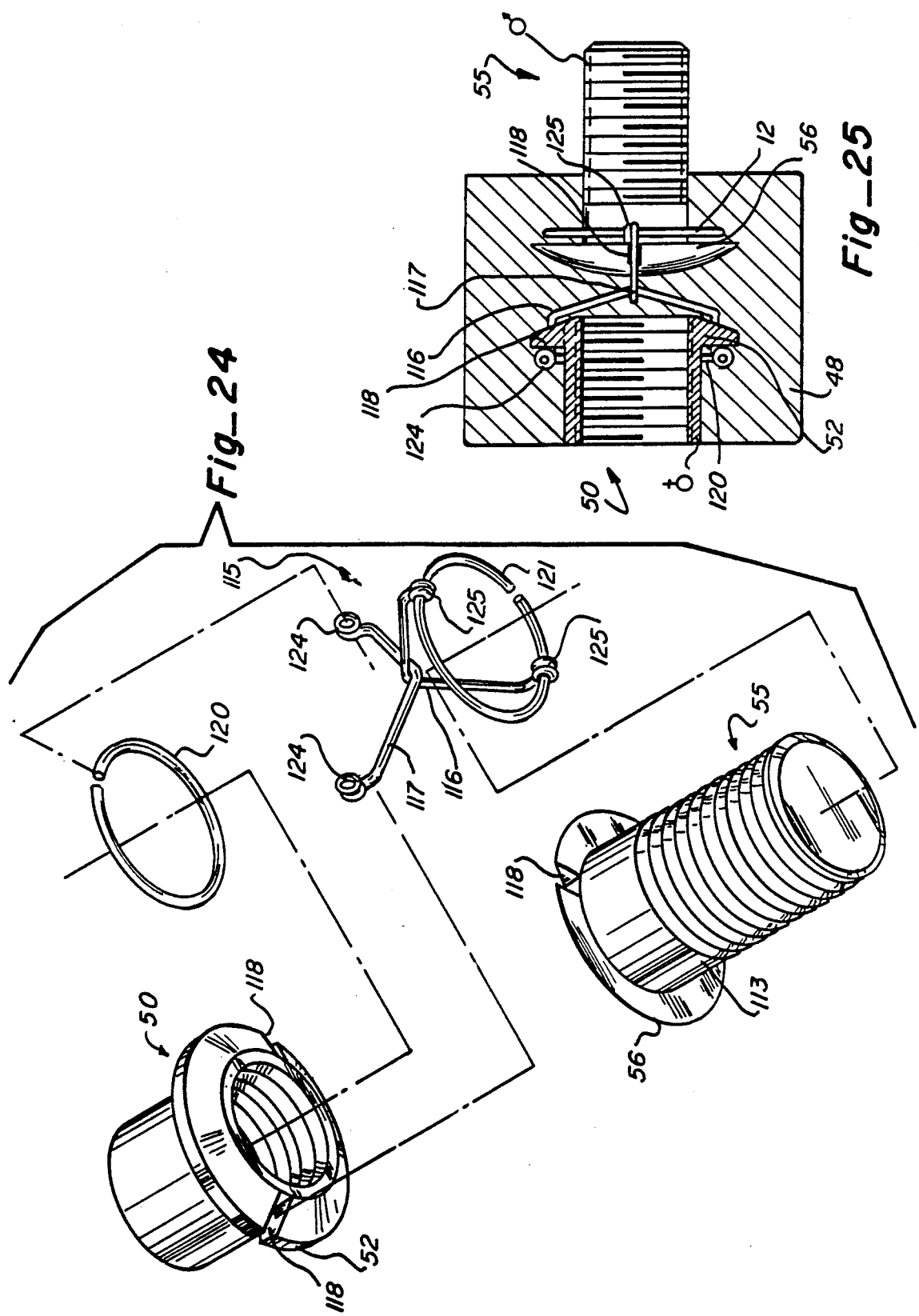

PROSTHETIC DEVICE FOR VIGOROUS ACTIVITIES

BACKGROUND OF THE INVENTION

The present invention relates generally to prosthetic devices and more particularly to prosthetic devices having flexing and shock absorbing capabilities for use in vigorous activities, such as atheletics and the like.

Amputees have many problems participating in active sports. For example, a person with a conventional hook type prosthetic hand ordinarily cannot participate in contact sports. There is a danger of causing physical trauma to the amputee's severed limb from the shock associated with physical contact. There is also a danger that the rigid hook will cause injury to others. Participation in sports such as gymnastics which require the use of the hands for balance is made difficult or impossible due to the fact that conventional prosthetic hands are not shaped to provide a stable platform. Additionally, conventional prosthetic hands are not capable of sufficient flexing to absorb shock and accomodate the rotation of the gymnast's hand relative to his or her arm during gymnastic maneuvers. Another problem relating to most sporting activities is the inability of existing prosthetic devices to store and release energy in a useful manner. Most existing prosthetic devices employ a cable system which is somewhat cumbersome and restricts the function, coordination, and timing necessary for athletics.

PRIOR ART

There are numerous prior art devices describing artificial hands of various shapes and construction; however, these devices may generally be placed within one of four categories. The first category consists of inactive terminal devices such as hooks. The second category might be described generally as artificial hands which seek to duplicate the grasping function of the opposed digits of an organic human hand. Such devices generally comprise opposed metallic jaw members which may be moved relative to one another to pick up or release a desired object. Such devices are "active" in that they are actuated by an external energy source, such as a cable or the like, in order to produce movement in the jaw members. Dorrance U.S. Pat. No. 1,271,448, McElroy U.S. Pat. No. 1,417,267 and Armstrong U.S. Pat. No. 1,423,296 are inventions of this type. Electromechanical or "bionic" hands which utilize an electrical energy source to provide movement of mechanical components constitute a third category which are also "active". Artificial hands in the fourth category might generally be described as those seeking to duplicate the appearance and "feel" of a natural human hand. Such devices generally are constructed from a resilient material simulating the texture of a natural hand and have a thumb and fingers simulating the external shape of a natural hand. In addition such devices may have an internal skelton made from wire, springs, or the like which in some cases may be bent to form various shapes and configurations. Such devices are generally referred to as "passive" since they are essentially immobile during ordinary use. Lucas U.S. Pat. No. 429,243, Broady U.S. Pat. No. 879,360, Ralston et al. U.S. Pat. No. 1,304,201, Everson U.S. Pat. No. 1,416,180, Hodgson U.S. Pat. No. 1,625,317, and Owen U.S. Pat. No. 1,893,714 are devices typical of the fourth category. There have been very few prosthetic devices which focus on duplicating the biomechanical functions performed by a natural limb during athletic activities. Those which do, deal primarily with devices useful on an artificial leg to reduce shock and torque transmitted to a leg stump by a prosthetic foot. Olowinski U.S. Pat. No. 3,706,465 discloses the use of two vane plates connected by compressible elastomeric bodies to produce an angular rotation in an artificial foot with respect to an artificial leg when a vertical load is experienced in the leg. Asbelle et al. U.S. Pat. No. 3,982,280, discloses a functional ankle for a prosthetic limb comprising a complex arrangement of cables, shock absorbers and block members interconnecting a prosthetic foot and shin member. Owens U.S. Pat. No. 3,947,897 discloses an apparatus for connecting a prosthesis to a bone of a stump of an amputated limb. The apparatus includes a tubular female socket adapter to be inserted within a inter medullary cavity of the bone. The tubular socket has an open lower end with a sleeve of biocompatible material permitting access through the skin of the amputees stump. The prosthesis has a contoured support for receiving the stump of the amputee. Wilson U.S. Pat. No. 4,134,159 discloses a torque absorber for a lower limb prosthesis which includes a retaining flange, forming a portion of an assembly rotatably mounted in a hollow cylinder member which may be adapted to receive a skeletal portion of a prosthesis. The resilient portion is bondingly formed about the hollow cylindrical member so that a plastomeric prosthetic socket may be bondingly molded to the resilient portion and the retaining flange for cooperation therebetween to allow limited rotational movement of the prosthetic socket relative to the hollow cylindrical member. Although a step in the right direction these devices are relatively complex and limited to particular applications with an artificial leg.

During normal athletic activities, a human limb is subject to flexing, twisting, and axial strain along multiple axes. The stresses which cause such strains may be generated by an external object such as, for example, the floor in a gymnastic routine, or the stresses may be generated by inertial forces within the limb itself such as the bending of the wrist in the followthrough of a baseball or golf swing. In a natural human limb, such stresses are absorbed by a complex interaction of cartilege, bone, flesh, and muscle tissue. It would be generally desireable to provide a prosthetic apparatus capable of duplicating this complex biomechanical function. It would also be desireable to provide a prosthetic apparatus capable of storing and releasing energy to duplicate functions performed by human muscles.

SUMMARY OF THE INVENTION

The prosthetic apparatus of the present invention comprises a flexible prosthetic hand constructed from an elastomeric material such as plastic or rubber having good resiliency characteristics. The hand has a generally scoop like shape comprising a finger portion, a palm portion, and a heel portion. The finger palm portion has one or more transverse pivot axes which allows the hand to be flexed about the pivot axes in either an inward (flexed) direction or an outward (extension) direction. The hand may be constructed with two pivot axes corresponding, approximately, to the second finger joint line and the finger-palm joint line of a natural human hand. The hand may be deformed under stress into the general shape of a human fist (flexed) or alternately stressed in the opposite direction to conform to the shape resembling a natural human hand with the fingers outstretched (extension) or bent backward with respect to the palm (hyper extension). The upper pivot axis corresponding generally to the second finger joints allows the upper finger portion to be bent initially with a smaller force than required to produce bending about the lower pivot axis. However, after the upper finger portion reaches a preselected angle of deflection about the upper axis, additional force will produce bending about the lower axis. Thus whether the finger portion of the hand is flexed or extended a force applied to the tip of the finger portion will produce segemented bending.

An advantage of this arrangement is that the relatively low stress bending of the upper finger joint allows the upper finger portion to absorb shocks without transmitting the force through the hand to the prosthetic arm. Another benefit from this arrangement is that the finger portion undergoes a relatively large angle deflection under even moderate loads. This allows a recoil force to be applied to an object over a sufficient time and distance to provide a degree of control. This characteristic is important in ball handling and the like in that it allows the user to control the direction in which the recoil energy is discharged and therefore allows the user to accurately control the ball or other object which caused the intial deflection of the finger portion. For example, if the prosthetic hand were being used to tip a basketball, the inertia of the basketball would initially cause the fingertip portion to deflect backward storing energy in the resilient material of the prosthetic hand. The energy is released as the hand recoils accelerating the basketball away from the fingertip portion.

The different torque requirements of the upper and lower bending axes also facilitate the use of the prosthetic hand as a stabilizing platform. For example, if the prosthetic hand were used to perform a handstand, the initial application of the hand to the floor would cause the upper finger portion to bend into a relatively straight line position relative the lower finger portion. Thereafter, the bending torque on the hand would be centered about the lower axis which would provide sufficient resistance to bending to hold a person stably in a handstand. If the gymnast were to convert the handstand into a forward flip, the recoil bending of the prosthetic hand would tend to complement the muscular force exerted by the natural hand. Although bending is concentrated in the two described bending axes of the prosthetic hand, the modulus of elasticity of the material is such that bending will take place, to some degree, throughout the entire hand in response to a stress force applied at any particular point. Thus the hand is universally deformable but will tend to assume the shape associated with a natural human hand under similar stress conditions. The hand may comprise an internal skeleton constructed of any suitable material to provide stiffening at a desired location. The prosthetic hand also includes an attachment means such as a male screw stud embedded in the elastomeric material in the heel of the hand to allow the hand to be connected directly to a prosthetic arm or alternatively to a second flexible prosthetic device.

One such device to which the hand might be connected is a joint module designed to duplicate the biomechanical function of a natural human wrist or other joint. The joint module is constructed from an elastomeric material similar to that used in the prosthetic hand and may be constructed in a variety of shapes, depending on the particular function to be performed by the joint. A cylindrical shape would generally allow the joint module to be bent or twisted in any direction whereas a joint module having an ovoid cross section would tend to bend more easily about its major axis. A joint module adapted for use as a wrist would have an attachment device at one end for mounting a prosthetic hand and a second attachment device at the opposite end for attachment to a conventional prosthetic arm. The two attachment devices are constructed of rigid material and are separated by a sufficient area of resilient material to allow universal bending, stretching, twisting, and compression of the joint module. Used in combination with the flexible prosthetic hand the joint module provides freedom of movement beyond that capable of the hand used by itself. Particular characteristics of any individual module depend on the length, diameter, and cross sectional shape of the module as well as the modulus elasticity and the durometer of the material from which it is constructed. A joint module of similar construction could be used to connect a prosthetic foot to a prosthetic leg with an appropriate cross section employed to limit lateral/medial rotation while allowing relatively greater dorsi-plantar flexion. A modified version of the joint module might be used as a knee module.

The prosthetic joint module, when used as a wrist module, may be connected to a prosthetic arm or may alternatively be connected to a prosthetic shock absorber device mounted on the prosthetic arm. Such a shock absorber device might also be used in conjunction with the prosthetic hand of the present invention without the joint module. It may also be used with any number of conventional prosthetic hands or other prosthetic members. The shock absorber device comprises a resilient body having a durometer somewhat higher than that of the material used in the flexible hand or joint module. The shock absorber resilient body has a generally cylindrical trunk portion adapted to fit into an aperture at the terminal end of a prosthetic limb. A radially extending plate portion of the resilient body is integrally formed with the trunk and positioned adjacent the planar surface at the terminal end of a prosthetic limb. It is attached thereto by suitable attachment means such as screws or the like. An attachment device, such as a female socket, is centrally positioned within the elastomeric body of the device and is essentially free floating therein. Thus in the case where a prosthetic hand is attached to the female socket of the shock absorber, a shock imparted to the hand and transmitted by the attachment portion of the hand to the female socket would cause the socket to be deflected within the resilient body of the shock absorber device. The energy imparted by the shock is absorbed by compression, twisting, and/or extention of the resilient body rather than being directly transmitted to the prosthetic limb. The shock absorber device may be equipped with conventional attachment means such as quick release mechanisms and the like to provide compatability with any prosthetic hand attachment member. The resilient body member of the shock absorber device may be constructed from a variety of materials to match the weight and strength of the user or to accomodate different activities.

A characteristic of the resilient materials employed in the prosthetic hand, joint module, and shock absorber device is an elastic memory which allows the resilient member to return to its original shape after deformation. Although the various components of the invention might be considered "passive" in that they contain no cables or external energy source, each component might also be considered "active" in the sense that it has a capability of storing and releasing energy whereby force may be applied to an external object.

Accordingly, it is an object of the present invention to provide a prosthetic apparatus which may be used for soccer, football, volleyball, basketball, martial arts, boxing, tumbling, tennis, golf, swimming, and many other vigorous activities. It is a further object of the invention to provide a prosthetic hand designed to flex under specific stress conditions in segmental portions. It is a further object of the invention to provide a prosthetic hand comprising a flexible internal skeleton. It is a further object on the invention to provide a prosthetic hand which may be provided with various prosthetic hand attachment means including screw stud attachment means and quick release stud attachment means. It is a further object of the invention to provide a prosthetic hand having a resilient external surface with gross and fine texture characteristics as required for particular athletic applications. It is a further object of the invention to provide a prosthetic hand capable of multiple directional flexing and shock absorption. It is a further object of the invention to provide a prosthetic hand capable of storing mechanical energy. It is a further object of the invention to provide a prosthetic hand capable of imparting recoil energy to an external object. It is a further object of the present invention to provide a prosthetic hand which may be constructed in a variety of shapes and sizes from materials of various elastomeric properties.

It is also among the objects of the present invention to provide a prosthetic joint module which may be used among other applications as a wrist module, ankle module, or knee module. It is a further object of the invention to provide a joint module which may be used in athletic and other vigorous activities. It is a further object of the invention to provide a joint module with omni-directional flex capabilities for providing a universal joint. It is a further object of the invention to provide a joint module which is capable of absorbing and dissipating shocks. It is a further object of the invention to provide a joint module which is capable of storing and releasing mechanical energy. It is a further object of the invention to provide a joint module which may be constructed in a variety of shapes and sizes and which may comprise materials of various elastomeric properties.

It is also among the objects of the present invention to provide a prosthetic shock absorber device which may be mounted on a terminal portion of a prosthetic limb to absorb shocks transmitted by a prosthetic hand or the like. It is a further object of the invention to provide a shock absorber device having attachment means substantially coaxial with the prosthetic limb and resiliently deflectable therewith. It is a further object of the invention to provide a shock absorber device which allows a person having a prosthetic hand to engage in various striking activities such as the use of an ax, bat, or golf club without traumatizing the terminal portion of the severed limb. It is a further object of the invention to provide a shock absorber device which may be constructed from materials of various elastomeric properties.

BRIEF DESCRIPTION OF THE DRAWINGS

Illustrative and presently preferred embodiments of the invention are shown in the accompanying drawing in which:

FIG. 1 is a perspective view of a prosthetic hand, prosthetic joint module, and shock absorber device mounted on a prosthetic arm.

FIG. 2 is a cross-sectional side elevation view of a prosthetic hand, prosthetic joint module, and shock absorber device;

FIG. 3 is a cross-sectional rear elevation view of a prosthetic hand, prosthetic joint module, and shock absorber device;

FIG. 4 is an exploded perspective view of a prosthetic, hand, prosthetic joint module, and shock absorber device;

FIG. 5 is a side elevation view of a prosthetic hand, prosthetic joint module, and shock absorber device used to perform a fist push-up;

FIG. 6 is a side elevation view of a prosthetic hand prosthetic joint module, and shock absorber device used to perform a palm push-up;

FIG. 7 is a side elevation view of a prosthetic hand, used to perform a finger push-up;

FIG. 8 is a perspective view of a prosthetic joint module;

FIG. 9 is a cut-away perspective view of a prosthetic joint module;

FIG. 10 is a perspective view of a female adapter;

FIG. 11 is a side elevation view of the female adapter of FIG. 10;

FIG. 12 is a perspective view of another embodiment of a female adapter;

FIG. 13 is a side elevation view of the female adapter of FIG. 12;

FIG. 14 is a side elevation view of a prosthetic joint module used to connect a prosthetic foot to a prosthetic leg;

FIG. 15 is a cross sectional view of an alternate embodiment of a prosthetic joint module;

FIG. 16 is a cross sectional view of yet another embodiment of a prosthetic joint module;

FIG. 17 is a cross-sectional view of still another embodiment of a prosthetic joint module;

FIG. 18 is a cut-away exploded perspective view of a shock absorber device;

FIG. 19 is a perspective view of another embodiment of a prosthetic joint module adapted to be used as a prosthetic knee module;

FIGS. 20-22 are side elevational views of a prosthetic hand, prosthetic joint module, and shock absorber device being used in ball handling;

FIG. 23 is a side elevation view of another embodiment of a prosthetic hand used with a prosthetic joint module and shock absorber device;

FIG. 24 is a side cross-sectional elevation view of another embodiment of a prosthetic joint module with elongation restraining apparatus attached to adapters; and FIG. 25 is an exploded perspective view of the restraining apparatus and adapters of the joint module of FIG. 24.

DETAILED DESCRIPTION OF THE INVENTION

Referring to FIG. 1 it may be seen that the prosthetic apparatus 10 of the present invention comprises a flexible hand 11, a wrist module 13, and a shock absorber device 16, mounted on a conventional prosthetic arm 18. As shown by FIGS. 1 through 4 the flexible hand 11 comprises a resilient hand scoop shaped member 20 having an external shape generally similar to that of a cupped human hand with the fingers held tightly together. The resilient member is formed from foam plastic, rubber or other resilient elastomeric material. The resilient hand member 20 like a natural human hand comprises a finger portion 22, a palm portion 23, and a heel portion 24; each portion forming a part of a continuous front surface 26, back surface 27 and lateral side surface 28. The front surface 26 is generally of a double concave shape having both a longitudinal and transverse arc of curvature producing the scoop shape referred to above. The back surface 27 has a generally double convex shape conforming to the double concave shape of the front surface 26. However the front and back surfaces 26, 27 converge along an arc from the heel portion 24 toward the terminal end of the finger portion 22 whereby the thickness of the hand member 20 diminishes from the heel 24 to the terminal end of the finger portion 22. As shown most clearly by FIGS. 2 and 3 the thickness of the lateral side surface 28 is substantially reduced in two areas corresponding roughly to the second finger joints and finger-palm connection joints of a natural human hand. The reduced area corresponding to the second finger joints of a human hand is produced by an indention 31 in the back surface 27 which forms a first bending axis CC. The area of the finger portion 22 between axis CC and the terminal end of the finger portion 34 will hereinafter be referred to as the upper finger portion 22A. A second indented area 32 in the back surface 27 produces a second bending axis DD corresponding generally to the fingers and palm connecting joints of a human hand. The area of the finger portion between axis CC and DD will hereinafter be referred to as the lower finger portion 22B. As shown by FIGS. 2 and 3 the heel 24 and palm 23 portions of the resilient member 20 have a longitudinal axis ZZ lying within a plane of bilateral symmetry (not shown) dividing the hand into equal left and right sections. The lower finger portion 22B has a longitudinal axis YY also lying within the plane of bilateral symmetry positioned at an acute angle "a" with respect to axis ZZ. The upper finger portion 22A has a longitudinal axis XX lying within the plane of bilateral symmetry and positioned at an acute angle "b" with respect to axis YY.

The resilient hand member 20 is attached to wrist module 13 by an attachment means embedded within the resilient material of the hand member 20. In the embodiment illustrated in FIGS. 2 and 3 the attachment means is a male stud adapter 37 comprising a stud member 40 protruding from the terminal end of the heel portion 24 which is integrally formed with a keeper means such as a radially extending flange 39 that acts as a deadman to prevent the adapter from being pulled out of the resilient material. The flange 39 may contain holes 41 which become impregnated with the resilient material while it is in a liquid forming state. The addition of holes 41 to the flange further aids in anchoring the male stud adapter and helps to prevent the adapter from breaking free of the resilient material as by twisting about the ZZ axis. The resilient hand member 20 may be provided with the desired resilient characteristics by a choice of the proper resilient material or laminated materials. The resilient member 20 may alternatively be provided with an internal skeleton 44 which serves to provide stiffness in the heel and palm portions 23, 24. The skeleton 44 may be allowed to float within the hand member 20 but is preferably mounted on the male stud adapter 37 as by longitudinal flange 42. The skeleton 44 may also be provided with holes 45 to stabilize and anchor the skeleton within the hand member 20. The skeleton 44 may be constructed of metal, high strength plastic, or any other material having suitable strength and resiliency characteristics.

The wrist module 13 may be more universally described as a joint module 12 because of its many possible substitution applications for various joints of the human body. As shown in FIG. 8 the joint module 12 has an elongate shape having a longitudinal axis FF. In the embodiment of FIGS. 8 and 9 the joint module 12 has a cylindrical cross section, however joint modules with various other cross sectional shapes may also be provided as illustrated by FIGS. 15 through 17. Referring again to FIGS. 8 and 9 it will be seen that the joint module 12 comprises two attachment means postioned at opposite ends of a resilient cylindrical joint member 48. Resilient joint member 48 is, like hand member 20, constructed of a resilient elastomeric material such as foam plastic, rubber, or the like. In the embodiment illustrated in FIGS. 8 and 9 the attachment means comprises a female adapter 50 having a threaded female socket 51 embedded within the joint member 48. The female adapter 50 may be provided with a radially extending flange member 52 fixedly mounted at one end thereof to anchor the adapter in the resilient joint member 48. A joint module male stud adapter 55 having a male stud member 54 protruding from the resilient member 48 and a radially extending flange 56 fixedly attached to an end portion of the stud member 54 is embedded within the resilient member 48 at the end opposite the female adapter 50. The flange portion 56 may also comprise holes 57 therein for the purpose of further anchoring the stud adapter 55 and preventing rotation thereof with respect to the resilient member 48. As shown by FIG. 9 the male stud adapter 55 and female adapter 50 are separated by a portion 58 of the resiliet member 48 whereby the two adapters 50, 55 may be displaced with respect to one another by deformation of the compressable member 48 without deformation of either adapter 50, 55. The female adapter 50 may be provided with a flange 52 having a rounded terminal surface 53 to allow the female flange 52 to "rock" with respect to the male flange 56 even when the resilient member 48 is compressed. Most of the bending deformation produced in the module will be centered in portion 58 and further discussion of the bending will be made in reference to perpendicular axes GG and HH positioned perpendicular to longitudinal axis FF at a point approximately midway between the two adapters 50, 55.

As shown by FIG. 14 the joint module 12 may function as an ankle module 14 to connect a prosthetic leg 92 to a prosthetic foot 94. In another embodiment of the invention as shown by FIG. 19 the joint module 12 may be rendered functional as a knee module 100 by inserting a pivot pin 106 in a bushing 103 affixed in a bore 107 coaxial with axis GG. Pin 106 is mounted in opposed holes 104 in the prongs 105 of a clevis 102. A clevis male stud member 108 threadably mounted in the clevis trunk portion 109 is adapted to mate with female adapter 50. Operation of the various embodiments of the joint module 12 will be discussed below.

The prosthetic shock absorber device 16 will now be described with reference to FIGS. 4, 18, and 10 through 13. As may be seen from FIG. 18, the shock absorber device 16 comprises a mushroom shape resilient body member 70 having an axially extending trunk portion 71 intregally connected with a radially extending plate portion 72. A shock absorber female adapter 74 having a threaded female socket portion 75 connected to a radially extending flange 76 is embedded in the resilient member 70 substantially coaxial with the longitudinal axis thereof. As illustrated by FIG. 10, 11 and 18 the flange portion 76 may comprise a rounded shape for the purpose of allowing the adapter 74 to rock relative to a planar surface at the base of the prosthetic arm internal cavity 87 in which the shock absorber device 16 is mounted. As shown by FIGS. 2, 3, and 18 the shock absorber device 16 may be provided with a stiffening ring 78 embedded in the resilient plate portion 72 in annular relationship with the female socket adapter 74. Axially aligned bores 80 in the resilient body plate portions 72 are coaxial with bores 79 in the stiffening ring 78 and may be aligned in coaxial relationship with bores 83 at the terminal end of the prosthetic arm 18. Shock absorber device 16 may be attached to the prosthetic arm 18 as by screws 81 with small washers 82 embedded for further strengthening within the resilient body plate portion 72 immediately below the stiffening ring bores 79. It may be seen from FIG. 18 that the internal cavity 87 of the prosthetic arm 18 has a diameter substantially equal to that of the outer diameter of the resilient member trunk portion 71. Thus any angular deflection of the female adapter 74 is resisted by the compression of the trunk portion 71 against the inner wall of the prosthetic arm cavity 87.

As shown by FIG. 18, an O-Ring groove 91 may be provided in the upper surface of plate portion 72 in circumscribing relationship with the open end of female adapter 74. An O-ring 93 may be frictionally or otherwise firmly embedded in the groove to provide a raised circular surface which will frictionally engage the terminal end of a prosthetic attachment to facilitate rotational adjustment thereof.

In an alternate embodiment a quick release female adapter 84, as shown in FIG. 12 and 13, may be used in place of the threaded socket female adapter 50, 74 of either the joint module 12 or shock absorber device 16 to make them compatible with a conventional quick release mechanism of a prosthetic hand. The quick release female adapter 84 comprises a female adapter plate 85 which is positioned in coplanar relationship with the outer surface of the particular resilient body 48, 70. A flange 89 having the shape of a truncated cone is rigidly attached in coaxial relationship with the female adapter plate 85 and may comprise holes 90 impregnated with resilient body member material to prevent to rotation of the quick release female adapter 84 with respect to the resilient body member 45, 70 in which it is embedded. Various other attachment devices may of course be employed to accommodate different attachment devices of prosthetic hands, wrists, joints, etc. and are within the scope of the invention. Particular functions of the prosthetic apparatus 10 and the various components thereof will now be described. It may be seen from FIGS. 1-4 that the shock absorber device 16, wrist module 13, and heel portion 24 of hand 11 are coaxial with axis ZZ when the prosthetic apparatus 10 is in an unstressed position. The lower finger portion 22B has a longitudinal axis YY positioned at an angle "a" with respect to axis ZZ equal to approximately 30 degrees. Fingertip portion 22A has an axis XX positioned at an angle "b" with respect to axis YY equal to approximately 15 degrees. Similar to a natural human hand and wrist, the prosthetic apparatus 10 is bendable, twistable, compressable, and stretchable in all directions, with bending of the hand 11 centered about transverse bending axes CC and DD. The torque required to produce a deformation about any particular portion of the apparatus 10 is dependant upon the durometer, modulus of elasticity and cross sectional area in that particular portion and is also dependant upon the placement of non resilient attachment members and skeleton members. Thus the characteristics of the prosthetic apparatus 10 may be changed by altering the shape or the composition of the resilient members. It may also be changed by use of various stiffening means embedded in the resilient members. The prosthetic apparatus 10 may be adapted to various requirements of the user based on considerations such as the user's body weight, the user's strength, and the type of activity in which the user will participate. Surface characteristics of the apparatus 10 may also be varied depending upon the particular use enviroment. For example, a waterproof surface may be employed if the device is to be used in swimming or water sports. A surface having a roughened frontal area 26 might be employed for aid in ball handling and the like. Alternate unstressed states might also be employed to allow the hand to perform specific functions such as grasping a baseball bat or golf club. As illustrated by FIG. 22 such a configuration might be provided by forming the hand resilient member 20 in a configuration wherein angle "a" is equal to approximately 90 degrees and angle "b" is on the order of 110 degrees. With such an arrangement a bat 19 or the like could be held by the frictional contact forces of the inwardly biased fingertip portion 22A, lower finger portion 22B, and palm portion 23. The male stud adapter 37 used in such a device might also be skewed (not shown) with respect to axis ZZ to allow the hand 11 to be properly aligned with the striking instrument.

For prosthetic apparatus 10 to be used in non-grasping activities such as ball handling as illustrated in FIGS. 20-22 or gymnastics as illustrated in FIGS. 5-7 it is generally desirable to provide bending axes CC, DD with characteristics whereby the upper finger portion 22A and lower finger portion 22B will deflect at different rates and different degrees in response to a force applied to the fingertip 34. The forces required to cause deformation of the apparatus 10 will be dependant upon the size and uses for which a particular apparatus 10 is designed. Parameters indicated in the below tables are representative of an embodiment of the apparatus 10 designed for all-around use by a vigorous individual approximately 6 feet in height, weighing approximately 150-160 pounds, with an amuatation approximately 5 inches below the elbow. The durometer of the hand flexible member 20 in this embodiment is approximatley 50A with a modulus of elasticity of approximately 200-250 psi. A similar or smaller unit might be appropriate for smaller, lighter individuals with similar amputations. A unit having heavier loading capabilities may be needed by larger individuals or for individuals with longer residual limbs. Of course, in actual use the segments of the hand 11 do not flex and extend separately but rather are integrally related.

TABLE A

Typical Dimensions of a Flexible Prosthetic Hand

| Segment Parameters | Upper Finger | Lower Finger | Palm-Heel |
|---|---|---|---|
| Cord Length | 1.46 inches (along XX Axis) | 1.57 inches (along YY Axis) | 3.16 inches (along ZZ Axis) |
| Width at Bending Axis | 2.63 inches (at CC axis) | 2.96 inches (at DD axis) | Not applicable |
| Thickness at Bending Axis | .70 inches (midline) .35 inches (edge) | 1.02 inches (midline) .65 inches (edge) | Not applicable |
| Thickness to width ratio at bending axis | 27% (midline) 14% (edge) | 35% (midline) 22% (edge) | Not applicable |
| Maximum width | 2.7 inches | 3.0 inches | 2.9 inches |

TABLE B

Typical Segmental Loading and Deflection About a Bending Axis With Remainder Of The Hand Held Rigid

| Deflection from Unloaded Static Position by a Force Applied at terminal end of heel perpendicular to the ZZ and bending axes | Pounds of Force Required Upper Finger Loading/ Bending about CC Axis | Pounds of Force Required Lower Finger Loading/ Bending about DD Axis |
|---|---|---|
| 15° Flexion | 5–10 | 20–30 |
| 30° Flexion | 20–25 | 30–40 |
| 60° Flexion | 25–35 | 40–50 |
| 90° Flexion | 40–50 | 55–60+ |
| 15° Extension | 10–15 | 15–20 |
| 30° Extension | 25–35 | 20–30 |
| 60° Extension | 35–40 | 40–50 |
| 90° Extension | 40–50 | 55–60+ |

TABLE C

Typical Dimensions for Wrist Module & Shock Absorber Device Having Circular Cross Sections

| | Length | Diameter |
|---|---|---|
| Wrist Module | 1.25 inches | 1.60 inches |
| Shock Absorber Device Plate | .34 inches | 2.00 inches |
| Shock Absorber Device Trunk | .34 inches | 1.25 inches |

The properties of the resilient members 20, 48, 70 used in the prosthetic hand 20, wrist module 12, and shock absorber device 16 may vary greatly depending upon particular use for which the prosthetic device is designed. Accordingly, the members may be constructed from a wide variety of materials including polyurethane, neoprene, and other natural and synthetic rubbers and plastic having varying capacities for shock dampening and energy storage. The modulus of elasticity of the resilient members 20, 48, 70 will generally fall within a range from 100 psi to 400 psi.

The durometer of the shock absorber device resilient body 70 is generally higher than the other members, measured in A-Scale Durometer, ranging from approximately 60 A to 80 A, but may range from 30 A to 90 A.

The durometer of a wrist module 12 may range from approximately 40 A to 75 A for a resilient member 48 having dimensions as described in Table C, but applications other than the wrist may require durometers from 30 A to 90 A. Higher durometer material would be used for example in handstands and other gymnastics. Lower durometer material might be used where greater flexibility is desired, such as in golf or baseball applications.

The durometer of the hand resilient member 20 will similarly range from about 30 A to 90 A but will usually comprise a range from approximately 30 A to 70 A. However, at lower durometers there may be a tendency for the resilient body member 48 of the wrist module 12 to tear. As shown by FIGS. 24 and 25, a restraining means 115 may be provided, such as interlocking wire members 116, 117 mounted in slots 118 on flanges 52, 56 of adapters 50, 55 and anchored thereto by means of circular wire rings 120, 121 in abutting engagement with the inward surfaces of said flanges 52, 56 and passing through looped portions 124, 125 at the ends of each wire member 116, 117. The restraining means 115 by restricting the longitudinal stretching of the resilient member 48, prevents tearing without substantially interfering with bending, twisting, or compression of the member 48. Other types of restraining means 115 such as a single strand of cable (not shown) connecting the adapters 50, 55 might also be used and are within the scope of the invention.

The characteristics of the prosthetic apparatus 10 will of course be altered by removal of any of the resilient components 11, 13 16. For example FIG. 7 illustrates the use of the flexible prosthetic hand 11 without the wrist module 13 and shock absorber 16. Similarly the shock absorber 16 might be used for shock reduction with a conventional prosthetic hand and the wrist module 13 might be employed as a joint module 12 in a number of different applications such as an ankle module 14 or knee module 100 as illustrated in FIG. 14 and 19 respectively.

Although the prosthetic apparatus 10 of the present invention may be considered passive in that it is not activated by cables or other attached energy sources it may act as a substitute for natural muscles by absorbing and releasing energy inherent in the relative motion of the apparatus 10 with respect to objects which it contacts. By appropriate motion of the user's arm, stored energy may be dissipated as by moving the apparatus 10 slowly away from the object. Or, the stored energy may be retransmitted to the object to produce a desired result such as acceleration of a ball as illustrated by FIGS. 20–22. Similarly the stored energy may be used to accelerate or support the user's body when the object contacted is a stationary surface such as a floor, wall, or balance beam, as illustrated in FIGS. 5–7. This second type of application may be particularly appreciated when the joint module 12 is used in the form of a knee module 100, illustrated in FIG. 19. In this application the clevis 102 which holds the resilient member 48 is attached to the terminal end of a thigh prothesis and the male stud adapter 54 at the lower end of the resilient member 48 is attached to an artificial leg apparatus. The lack of bending energy at a knee joint has been an acute problem in the use of artificial legs. For example, when a person sits down in a chair the force required to again assume an erect position must be generated entirely by the natural limb. When the knee module 100 of the present invention is used the resilient member 48 stores energy generated by the displacement of the person's body from a raised to a lowered position. When the person desires to stand the resilient member supplies torque which helps the person to raise his body from the lowered position. Similarly, when a person is walking or running the resilient member 48 is deformed by the weight transfered to it when the foot first makes contact with the walking surface. As the person's body moves forward with respect to the foot the resilient member straightens out, tending to accelerate the person forward. Interchangeable resilient members of various shapes may be used to accomodate the demands of different activities.

It is contemplated that the inventive concepts herein disclosed may be variously otherwise embodied and it is intended that the appended claims be construed to include alternative embodiments of the invention except insofar as limited by the prior art.

What is claimed is:

1. A prosthetic hand mountable on a terminal portion of a prosthetic limb apparatus for use in athletic activities and the like for simulating certain dynamic biomechanical functions of a natural hand comprising:
   (a) a resilient one piece integrally formed scoop-shaped member comprising an integral unit finger portion, a palm portion and a heel portion which together provide a continuous front surface, back surface and peripheral edge surface, said member having an elastic memory and being movable under load between a normal unstressed state and a plurality of relatively large deformation stressingly deformed states by elastic deformation to enable said member to absorb energy in transformation from said unstressed state to said stressingly deformed states and to release energy in a controllable form during elastic transformation from said stressingly deformed states to said unstressed state; and
   (b) attachment means embedded in said member for removably mounting said resilient member on the prosthetic limb apparatus.

2. The prosthetic hand of claim 1 wherein said resilient member comprises at least one transverse bending axis whereby bending deformation of said member is proportionately greatest about said axis and whereby said scoop-shaped member is elastically foldable about said transverse bending axis in both an extension direction and a flexion direction through an angle of deflection of at least 30°.

3. The prosthetic hand of claim 2 wherein said attachment means is embedded in said heel portion of said resilient member.

4. The prosthetic hand of claim 3 wherein said resilient member comprises a first transverse bending axis positioned at an intermediate location on said finger portion; and
   a second transverse bending axis positioned proximate the connection of said finger portion and said palm portion, whereby said finger portion is divided into an upper finger section extending from said first bending axis to the terminal end of said finger portion and a lower finger section extending between said bending axes.

5. The prosthetic hand of claim 4 wherein said first and second transverse bending axes are positioned in areas of reduced cross section and wherein said first transverse bending axis comprises an area of smaller cross section than said second transverse bending axis whereby a force exerted at the terminal end of said finger portion normal said axes will produce a substantially greater deflection about said first transverse bending axis than about said second transverse bending axis.

6. The prosthetic hand of claim 5 wherein said front surface of said finger portion and said palm portion comprises a continuous substantially double concave surface having first longitudinal and first transverse axes of curvature and wherein said back surface of said finger portion and said palm portion comprise a continuous substantially double convex surface having second longitudinal and second transverse axes of curvature.

7. The prosthetic hand of claim 6 wherein said finger portion decreases in thickness from the point of connection of said palm portion to the terminal end of said finger portion, and wherein said scoop-shaped member decreases in thickness from the center thereof to the lateral sides thereof, whereby peripheral portions of said scoop-shaped member dissipate shocks.

8. The prosthetic hand of claim 5, wherein said attachment means comprises a male stud adapter embedded in said heel portion of said resilient member and longitudinally protruding therefrom.

9. The prosthetic hand of claim 8 wherein said male stud adapter comprises annular flange means positioned about an embedded portion of said male stud adapter for maintaining said adapter in said resilient member.

10. The prosthetic hand of claim 9 wherein said flange means comprises holes therein for improving the bonding of said flange means to said resilient member.

11. The prosthetic hand of claim 1, 5 or 10 wherein said resilient member comprises an elastomeric material having a durometer comprising a range from 30 A to 90 A.

12. The prosthetic hand of claim 5 further comprising:
   skeleton means for stiffening a portion of said resilient member embedded within said resilient member.

* * * * *